(12) United States Patent
Sibik et al.

(10) Patent No.: US 11,454,609 B2
(45) Date of Patent: *Sep. 27, 2022

(54) USE OF A SOLID FRACTION SENSOR TO EVALUATE A SOLID FRACTION OF A TARGET PHARMACEUTICAL SAMPLE AND SOLID FRACTION SENSOR

(71) Applicant: HOFFMANN-LA ROCHE INC., Little Falls, NJ (US)

(72) Inventors: Juraj Sibik, Basel (CH); Pascal Chalus, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 144 days.

This patent is subject to a terminal disclaimer.

(21) Appl. No.: 16/648,806

(22) PCT Filed: Sep. 21, 2018

(86) PCT No.: PCT/EP2018/075637
§ 371 (c)(1),
(2) Date: Mar. 19, 2020

(87) PCT Pub. No.: WO2019/057910
PCT Pub. Date: Mar. 28, 2019

(65) Prior Publication Data
US 2020/0217811 A1 Jul. 9, 2020

(30) Foreign Application Priority Data

Sep. 21, 2017 (EP) .................................. 17192404.6

(51) Int. Cl.
*G01N 27/22* (2006.01)
*G01N 33/15* (2006.01)
(Continued)

(52) U.S. Cl.
CPC ......... *G01N 27/221* (2013.01); *G01N 27/121* (2013.01); *G01N 33/15* (2013.01); *G01F 17/00* (2013.01); *G01N 21/3563* (2013.01)

(58) Field of Classification Search
CPC .. G01N 27/221; G01N 33/15; G01N 21/9508; G01N 21/3563; G01N 27/121; A61J 3/10; B30B 11/005; G01F 17/00
See application file for complete search history.

(56) References Cited

U.S. PATENT DOCUMENTS

| 4,461,363 A | 7/1984 | Loy |
| 5,135,113 A | 8/1992 | Mayer et al. |

(Continued)

FOREIGN PATENT DOCUMENTS

| CA | 2308212 A | 3/2000 |
| DE | 25 02 098 A1 | 8/1975 |

(Continued)

OTHER PUBLICATIONS

International Search Report dated Nov. 16, 2018 in corresponding International Patent Application No. PCT/EP2018/075637.
(Continued)

*Primary Examiner* — Amy He
(74) *Attorney, Agent, or Firm* — Medler Ferro Woodhouse & Mills PLLC

(57) ABSTRACT

A method of evaluating a solid fraction of a target pharmaceutical sample by means of a solid fraction sensor is disclosed with the solid fraction sensor including a first conductor element, a second conductor element, an operation space and an energy source arranged to generate an electric field in the operation space by means of the first conductor element and the second conductor element. The method including positioning the target pharmaceutical sample in the operation space of the solid fraction sensor,
(Continued)

determining a capacitance between the first and second conductor element with the target pharmaceutical sample located in the operation space, and converting the determined capacitance together with information about a composition of a reference pharmaceutical sample having the essentially same dielectric properties as the target pharmaceutical sample and about a thickness of the reference pharmaceutical sample into a solid fraction of the target pharmaceutical sample.

27 Claims, 3 Drawing Sheets

(51) Int. Cl.
*G01N 27/12* (2006.01)
*G01N 21/3563* (2014.01)
*G01F 17/00* (2006.01)

(56) References Cited

U.S. PATENT DOCUMENTS

| | | |
|---|---|---|
| 7,541,816 B1 | 6/2009 | Liao et al. |
| 2009/0026373 A1 | 1/2009 | Mertens et al. |
| 2009/0237090 A1 | 9/2009 | Alimi et al. |
| 2012/0112817 A1 | 5/2012 | Yannick et al. |
| 2013/0099804 A1 | 4/2013 | Kim |
| 2013/0284930 A1 | 10/2013 | Kato |

FOREIGN PATENT DOCUMENTS

| | | |
|---|---|---|
| JP | 2000074757 A | 3/2000 |
| JP | 2007256267 A | 10/2007 |
| JP | 2011512245 A | 4/2011 |
| JP | 2013228241 A | 11/2013 |
| JP | 2016108995 A | 6/2016 |
| WO | 200014522 A | 3/2000 |
| WO | 2009097502 A | 8/2009 |

OTHER PUBLICATIONS

Visotec GmbH "VisioAMV Advanced Mass Verification for powders, solids & liquids", Sep. 1, 2016, pp. 1-2, XP055416565, www.visiotec.info/productstrending/visioamv/#c39.

Japanese Office Action issued in corresponding Japanese Patent Application No. 2020-515901 dated May 31, 2022.

USE OF A SOLID FRACTION SENSOR TO EVALUATE A SOLID FRACTION OF A TARGET PHARMACEUTICAL SAMPLE AND SOLID FRACTION SENSOR

TECHNICAL FIELD

The present invention relates to a use of a solid fraction sensor to evaluate a solid fraction of a target pharmaceutical sample and furthermore it relates to a solid fraction sensor.

BACKGROUND ART

Porosity of solids has a tremendous effect on their mechanical properties and is hence of importance in many industries, including pharmaceutical, chemical or food industry. In pharmaceutical manufacturing, porosity of the intermediates influences also the porosity of the final solid dosage forms, while the porosity of the final dosage forms influence their disintegration and dissolution behaviour. Hence, porosity of the intermediates and final dosage forms plays an important role in the bioavailability of pharmaceutical products.

The intermediate porosity is of particular importance in dry granulation of powder mixtures via roller compaction and in tablet pressing. In roller compaction, the powder mixture is first pressed into a ribbon using two spinning rolls and the ribbon is then milled into granules. For example, U.S. Pat. No. 5,509,612 A describes a roller compaction device for the continuous shaping of particulate materials.

Using too small compaction force during the roller compaction can result in fragile granules and high content of small granules, with only limited improvement in the flowability and prevention of segregation in comparison to the input powder mixture. On the other hand, too large compaction force would take away significant part of compressibility of the powder and prohibit further pressing into tablet. Knowledge of ribbon porosity can serve as a good indication for both granule size and tablet mechanical properties of a target pharmaceutical sample. In tablets, too high porosity will likely result in chipping and breaking of the tablet, while too low porosity may negatively affect the release of the drug substance from the tablet.

Commonly, the porosity of solid state intermediates and final products is determined by off-line analysis. When the true density is known, the bulk porosity can be determined by simple measurements of weight and bulk volume. For more accurate determination of volume for a sample with uneven thickness one often uses surface scanning laser confocal displacement meter. On the other hand, technologies like pycnometry can provide absolute measure of porosity and pore distribution without any prior knowledge, although at a higher labour cost.

Further, there is an on-going search for suitable process analytical technologies (PAT) around manufacturing pharmaceutical products and their intermediates. In particular, it is aimed to achieve processing without any interruption such that the above off-line analysis typically is not appropriate. In this context, some earlier proposals considered utilization of NIR spectroscopy, a common PAT tool which is sensitive to both chemical and physical properties of the sample. However, NIR provides an indirect measure of porosity based on a somewhat impractical multivariate calibration and it is not trivial to isolate the undesired chemical and other physical effects in the porosity prediction. Terahertz spectroscopy provides a more accurate and easier to calibrate alternative, but is still relatively new to pharmaceutical industry and requires further design for implementation as PAT tool.

Recently, a novel low-cost measurement based on thermal imaging has been proposed as a solution for ribbon porosity analysis during roller compaction. It is however suitable only for the ribbons of sufficient quality and it requires careful consideration of environmental effects. All of the aforementioned techniques are however still comparably difficult to adapt for inline/online automated measurements that could be used as process analytical technology.

Therefore, an object of the invention is to propose a technique or system allowing to evaluate properties of a pharmaceutical sample, such as its porosity, density or the like, which is suitable for inline/online automated measurements.

DISCLOSURE OF THE INVENTION

According to the invention this need is settled by use of a solid fraction sensor to evaluate a solid fraction of a target pharmaceutical sample as defined by various embodiments described herein and by a solid fraction sensor as defined by various embodiments described herein.

In particular, in one aspect of the invention, a use of a solid fraction sensor to evaluate a solid fraction of a target pharmaceutical sample is proposed. The solid fraction sensor comprises a first conductor element, a second conductor element, an operation space and an energy source arranged to generate an electric field in the operation space by means of the first conductor element and the second conductor element. The use according to the invention comprises: positioning the target pharmaceutical sample in the operation space of the solid fraction sensor; determining a capacitance between the first and second conductor element with the target pharmaceutical sample located in the operation space; and converting the determined capacitance together with information about a composition of a reference pharmaceutical sample having the essentially same dielectric properties as the target pharmaceutical sample and about a thickness of the reference pharmaceutical sample into a solid fraction of the target pharmaceutical sample. Thus, the use can include that the target pharmaceutical sample is exposed to the electric field in the operation space of the solid fraction sensor for determining a capacitance between the first and second conductor element with the target pharmaceutical sample located in the operation space.

The information about the reference pharmaceutical sample can be or comprise solid fraction data or any other data about its composition. Particularly, it comprises permittivity of the reference pharmaceutical sample and a solid fraction ratio of the reference pharmaceutical sample. Generally, permittivity ($\varepsilon$) or dielectric permittivity can be a measure of resistance that is encountered when forming an electric field in a medium. Relative permittivity can be the factor by which an electric field between charges is decreased relative to vacuum. More specifically, $\varepsilon$ can describe the amount of charge needed to generate one unit of electric flux in the medium. Accordingly, a charge will yield more electric flux in a medium with low $\varepsilon$ than in a medium with high $\varepsilon$. Thus, $\varepsilon$ is the measure of a material's ability to resist an electric field rather than its ability to permit it. Typically, $\varepsilon$ is specified in Farad per meter (F/m). Such information allows an efficient and accurate evaluation of the solid fraction of the target pharmaceutical sample.

Thereby, the information about the composition of the reference pharmaceutical sample and about the thickness of the reference pharmaceutical sample comprises pairs of permittivity and corresponding solid fraction ratio. With such pairs, the permittivity and solid fraction ratio can efficiently be interrelated. In particular, the information about the composition of the reference pharmaceutical sample and about the thickness of the reference pharmaceutical sample preferably is a calibration curve. Such a calibration curve allows for an efficient and reproducible evaluation. More specifically, by providing a plurality of pairs of permittivity and corresponding solid fraction ratio and, particularly a representative number of pairs of permittivity and corresponding solid fraction ratio, solid fraction can be determined in a comparably broad range such as, for example, in a full range from 0% to 100%. Thus, the plurality of such pairs or the calibration curve allows for covering the full range particularly also in cases where non-linear calibration curves or a non-linear permittivity to solid fraction relation distributions are involved.

The target pharmaceutical sample can particularly be a drug, a pharmaceutical substance, a component thereof or an intermediate substance involved in a process of manufacturing a pharmaceutical substance or drug product. Also, it can be a formulation only including one or more excipients and/or other auxiliary ingredients such as, e.g., a placebo sample.

The term "drug" as used herein can relate to a therapeutically active agent, also commonly called active pharmaceutical ingredient (API), as well as to a combination of plural such therapeutically active substances. The term also encompasses diagnostic or imaging agents, like for example contrast agents (e.g. MRI contrast agents), tracers (e.g. PET tracers) and hormones, that need to be administered in liquid form to a patient.

The term "pharmaceutical substance" as used herein can relate to a drug as defined above formulated or reconstituted in a form that is suitable for administration to the patient. For example, besides the drug, a pharmaceutical substance may additionally comprise an excipient and/or other auxiliary ingredients.

The term "drug product" as used herein can relate to a finished end product, comprising a pharmaceutical substance or a plurality of pharmaceutical substances. In particular, a drug product may be a ready to use product having the pharmaceutical substance in an appropriate dosage and/or in an appropriate form for administration. For example, a drug product may include an administration device such as a prefilled syringe or the like.

The reference pharmaceutical sample can particularly be similar to the target pharmaceutical sample wherein, besides the essentially same dielectric properties, the samples can have the same API and/or the essentially same chemistry and/or the essentially same composition.

With the use of the solid fraction sensor according to the invention, it is possible to measure the change in the capacitance of the solid fraction sensor induced by the presence of the target pharmaceutical sample. The knowledge of the solid fraction sensor geometry, the target pharmaceutical sample geometry and the capacitance change can be used to extract the real part of a dielectric permittivity of the target pharmaceutical sample. The measured dielectric permittivity can be calibrated with respect to the target pharmaceutical sample solid fraction by comparing it to the information about the composition of the reference pharmaceutical sample, allowing a current dielectric sensor to be used as a solid fraction sensor. Like this, an actual value of the solid fraction of the target pharmaceutical sample can be determined in a comparably broad range of values.

This setup or use offers significant practical advantages in comparison to state of the art methods, namely: it is applicable both off-line/at-line as well as inline/online measurement; no electrical contact with the target pharmaceutical sample is needed; and a sensitivity of around less than 3% absolute solid fraction deviation can be achieved. In addition, the possible read-out time can be less than 10 ms, which is fast enough for the desired inline/online application. The use of the current solid fraction sensor can show a good linearity in the target range of interest between 50% and 100% solid fraction for pharmaceutical intermediates and products, such as ribbons and tablets. Furthermore, the measurement can be robust, because it shows low impact of e.g. a product lamination or a product fractionation of the target pharmaceutical sample. Still further, in the setup according to the invention it can be prevented that an electrical contact is required between the target pharmaceutical sample and the first or second conductor element.

By using the capacitance for calculating the solid fraction it can be achieved that only a part of an object or the target pharmaceutical sample is measured. As some known solid fraction determination processes are based on proportionality of solid fraction and weight, only solid fraction of complete objects can be determined in these processes. However, particularly for applications where comparably large samples, continuous samples and/or non-uniform samples such as samples having a varying thickness are involved, in accordance with the use according to the invention solid fraction of a portion of the target pharmaceutical sample can be determined which allows for determination of solid fraction of such samples or for determining a solid fraction distribution or solid fraction mapping and the like.

For an appropriate functioning, the solid fraction sensor preferably is electromagnetically shielded. Like this, disturbances induced by other parts of the manufacturing installation or still other things can be prevented or minimized.

In one preferred embodiment, the target pharmaceutical sample is bounded. Such a bounded pharmaceutical sample can be a compressed substance such as a tablet, or a ribbon which is further processed to granules or the like, or otherwise bounded such as by lyophilisation. In another preferred embodiment, the target pharmaceutical sample is unbounded. Such a sample can, e.g., be a lyophilized powder, any loose powdered material or the like.

Advantageously, the use comprises adjusting a strength of the electric field in the operation space.

In some applications, it can be advantageous to determine the capacitance by a capacitance-to-digital conversion, particularly, by applying a sigma-delta modulation. Like this, the solid fraction sensor can be embodied as a Capacitance to Digital Converter (CDC) or sigma-delta CDC. With a sigma-delta CDC the invention can be realised comparably inexpensive and can have a strong potential as a process analytical technology (PAT) in solid product manufacturing in general and especially in the pharmaceutical industry. Furthermore, it allows determining capacitance or capacitance changes at a comparably low scale such as in a Femto-Farad (fF) range. Like this, a comparably high accuracy or high sensitivity (fF) can be achieved.

In other applications, it can be beneficial to use a charge-balancing circuit to measure the capacitance. Such capacitance measurement can be suitable accurate and fast to be implemented online in a pharmaceutical manufacturing process.

In still other applications, a discharge time can be measured and the capacitance can be determined by using the measured discharge time. For example, the measurement of the discharge time can be provided by a PICO CAP converter. Such technique can particularly provide for a suitable accuracy of the capacitance determination.

Also, a time based determination can be applied in which, typically, an unknown capacitance is used to modify an oscillator circuit frequency. Or, a bridge determination can be used in which two voltage dividers are compared wherein one path is known and the other one comprises the unknown capacitance.

Preferably, the at least one of the first conductor element and the second conductor element is displaced to adjust the operation space. Like this, for example, it can be achieved that the conductor elements preferably slightly contact an object arranged in the operation space. Thereby, the occurrence of free space between the conductor elements and the object can be reduced or minimized such that the accuracy of the solid fraction determination can be increased or optimized, since best results of the capacitance measurement may be achieved, when an air gap between the target pharmaceutical sample and one of the first and/or second conductor element is as small as possible.

When determining the solid fraction of the target pharmaceutical sample, in general, any geometrical difference, composition difference and moisture content difference between the reference pharmaceutical sample and the target pharmaceutical sample should be accounted for in order to achieve a high accuracy. For example, surface pattern, e.g. caused by ribbons produced with patterned rolls while the reference pharmaceutical sample may be produced without, may occur which can influence the accuracy of the solid fraction determination. Non-variable differences can be accounted for by correction of the measured signal prior comparison with the calibration curve or calibration data. One option is to include as many such dependencies in the multi-variate calibration curve or calibration data as feasible. However, this could be comparably cumbersome as it might cause and extensive calibration requirement.

For those properties that are more or less constant such as, e.g., moisture content, some of the dimensions and the like, the accuracy lowering effects may be reduced by choosing a suitable reference pharmaceutical sample that matches the properties of the target pharmaceutical sample and measured at operating conditions. When this is impractical, it might be tried to account for them in the evaluation of the reference pharmaceutical sample such as, e.g., surface pattern can be accounted for instead of forcing the reference pharmaceutical sample having the same surface pattern. When the sample properties varies it might be beneficial to provide active correction by having independent measure of the variable properties. Once such properties are measured, they can be accounted for numerically instead of having multi-variate calibration.

In this context, for an accurate evaluation of the solid fraction, it can be beneficial to further measure a thickness of the target pharmaceutical sample positioned in the operation space. Thereby, the thickness can measured by any suitable measurement arrangement such as an electrical, mechanical, optical, acoustic, distance capacitance or combined sensor.

In a preferred embodiment, the use according to the invention further comprises: positioning the target pharmaceutical sample in a further operation space of the solid fraction sensor or a further solid fraction sensor, having a further first conductor element, a further second conductor element, the further operation space and a further energy source arranged to generate an electric field in the further operation space by means of the further first conductor element and the further second conductor element; determining a further capacitance of the target pharmaceutical sample located in the further operation space; converting the determined further capacitance together with the information about the composition of the reference pharmaceutical sample and about the thickness of the reference pharmaceutical sample into a further solid fraction of the target pharmaceutical sample; and determining a solid fraction distribution of the solid fraction of the target pharmaceutical sample and the further solid fraction of the target pharmaceutical sample. Particularly, when comparably large and/or comparably inhomogeneous target pharmaceutical samples are involved, such determination of the solid fraction distribution can be beneficial for achieving a complete or sufficient evaluation of the target pharmaceutical sample.

Thereby, the operation space and the further operation space preferably are positioned neighbouring each other such that, particularly, different parts of the target pharmaceutical sample are involved when determining the capacitance and the further capacitance of the target pharmaceutical sample. Like this, the solid fraction distribution can be determined by two adjacent capacitors established by the neighbouring operation spaces such that different parts of the target pharmaceutical sample can be involved. Also, the solid fraction distribution can be determined by a multi operation space array employing the principles of electrical capacitance tomography.

Preferably, the operation space and the further operation space are positioned separate from each other such that the target pharmaceutical sample is arranged in the operation space and the further operation space when determining the capacitance and the further capacitance of the target pharmaceutical sample. With such arrangement an improved solid fraction distribution determination may be achieved.

In a further preferred embodiment, the use according to the invention comprises: positioning the target pharmaceutical sample in a reference operation space of a reference solid fraction sensor having a reference first conductor element, a reference second conductor element, the reference operation space and a reference energy source arranged to generate an electric field in the reference operation space by means of the reference first conductor element and the reference second conductor element; determining a reference capacitance of the target pharmaceutical sample located in the reference operation space; converting the determined reference capacitance together with the information about the composition of the reference pharmaceutical sample and about the thickness of the reference pharmaceutical sample into a reference solid fraction of the target pharmaceutical sample; and comparing the solid fraction of the target pharmaceutical sample to the reference solid fraction of the target pharmaceutical sample in its solid state. Like this, the quality and accuracy of the sensing procedure can be increased.

Preferably, the use comprises a step of measuring a distance between the first and second conductor elements. By measuring the distance between the conductor elements, which can be the width of the gap between the two, the thickness or also another dimension of the target pharmaceutical sample can be determined. In particular, when a compression or other shaping of the target pharmaceutical sample between the first and second conductor elements is involved, such measuring allows for efficiently gathering information about the thickness of the target pharmaceutical sample, which can be used for converting the determined capacitance.

In a preferred embodiment, at least one of the first and second conductor elements is a roll of a roll press arrangement. The roll press arrangement can be a roller compactor for pressing a powder mixture of the target pharmaceutical sample into a ribbon. A typical roller compactor can comprise two rolls, which press the powder into the ribbon. By embodying at least one of the rolls to be displaced towards the other roll a thickness of the ribbon can be defined or adjusted. Therefore, the displacable roll may achieve to measure or determine the thickness of the target pharmaceutical sample. The ribbon can then be milled into granules.

By determining the distance between the first and second conductor elements via adjusting the operation space by displacing the at least one of the first conductor element and the second conductor element and/or via measuring the distance between the first and second conductor elements, the distance or gap between the first and second conductor elements can be used to estimate or determine the thickness of the target pharmaceutical sample. When adjusting the operation space or gap between the conductor elements by displacing one of the conductor elements, e.g. in form of a roll, a pre-determined expansion coefficient of the target pharmaceutical sample can be considered or involved in order to estimate the thickness of the target pharmaceutical sample. This can particularly be beneficial for pharmaceutical materials with elastic properties which may expand significantly after compression.

In another aspect of the invention, a solid fraction sensor is proposed, which comprises a first conductor element, a second conductor element, an operation space, an energy source arranged to generate an electric field in the operation space by means of the first conductor element and the second conductor element, and a controller adapted to determine a capacitance between the first and second conductor element with a target pharmaceutical sample located in the operation space. The controller comprises calibration data of a reference pharmaceutical sample having the essentially same dielectric properties as the target pharmaceutical sample, the calibration data comprises composition data about the composition of the reference pharmaceutical sample and thickness data or geometry data about the thickness or the geometry of the reference pharmaceutical sample, the controller is adapted to convert the calibration data and the determined capacitance into solid fraction data of the target pharmaceutical sample, and the controller is adapted to generate a solid fraction signal representing the solid fraction data. The solid fraction signal can be in any suitable form such that information about the solid fraction, i.e. the solid fraction data, is represented. For example, the signal can be an electrical signal, a ultrasonic or other acoustic signal, a (laser) light signal or the like.

The solid fraction sensor according to the invention and its preferred embodiments described below allow for efficiently achieving the effects and benefits described above in connection with the use according to the invention and the embodiments thereof.

Preferably, the energy source of the solid fraction sensor is connected to at least one of the first conductor element and the second conductor element. This allows for an efficient implementation of the sensor. In the same context, the controller preferably is adapted to adjust a strength of the electric field in the operation space.

Preferably, the controller of the solid fraction sensor has a data storage in which the calibration data is stored. The data storage can be any suitable permanent or volatile data storage such as, e.g., a flash memory, a hard disk, a memory chip, an external storage or cloud storage, or the like.

The calibration data can comprise a permittivity of the reference pharmaceutical sample and a solid fraction ratio of the reference pharmaceutical sample or pairs of permittivity and corresponding solid fraction ratio or the calibration data can be or comprise a calibration curve.

The first and second conductors can be made of any suitable conductive material. They can further have any predefined shape or geometry. However, in a preferred and comparably simple embodiment, the first conductor element and the second conductor element are metallic and plate-like shaped. The term "plate-like" as used herein can relate to a plate being straight, even or bent. It can also relate to a plane, structured or uneven plate. Such plates allow for easily defining the operation space in between themselves which can efficiently be evaluated since the well defined and eventually simple geometry. In a specific example, the first conductor element can be provided in form of a roll of a roller compactor for pressing a powder mixture of the target pharmaceutical sample into a ribbon, while the second conductor element can be a curved segment, which limits the operation space between both conductor elements.

In a preferred embodiment of the solid fraction sensor according to the invention, the controller is adapted to determine the capacitance by a capacitance-to-digital conversion and, more specifically, it can be adapted to apply sigma-delta modulation to determine the capacitance.

In another embodiment of the of the solid fraction sensor according to the invention, the controller is adapted to measure a discharge time and to determine the capacitance by using the measured discharge time. For example, the solid fraction sensor can be implemented as or comprise a PICO-CAP converter.

In still another embodiment of the of the solid fraction sensor according to the invention, the controller is adapted to determine the capacitance by using the charge-balancing method or a charge balancing circuit.

For adjusting the gap between the first and the second conductor element or for adjusting the size of the operation space, respectively, the solid fraction sensor preferably comprises a displacement structure, wherein at least one of the first conductor element and the second conductor element is mounted to the displacement structure such that the first conductor element and the second conductor element are movable relative to each other. The displacement structure allows the adjustment of an air-gap in the operation space to a minimum such that the accuracy of the solid fraction determination can be increased or optimized.

The operation space of the solid fraction sensor can be a space in which the first and second conductor elements may generate an electric field. For example, the first and second conductor elements may be positioned aside each other such that the operating space is located above or below the two conductor elements where the electric field can be generated. However, preferably, the solid fraction sensor is embodied such that the operation space is a gap separating the first conductor element and the second conductor element. Such a gap allows for well defining the operation space which makes the determination of the capacitance comparable simple and efficient.

In a preferred embodiment, the solid fraction sensor comprises a thickness measuring unit adapted to measure a thickness of the target pharmaceutical sample, preferably, when positioned in the operation space. The thickness measuring unit can be any suitable measurement arrangement such as an electrical, mechanical, optical, acoustic or combined sensor. However, preferably, the thickness measuring sensor has a distance capacitance sensor. Such arrangement allows for determining the thickness of the target pharmaceutical sample by the same or similar means of principles applied for determining the capacitance.

Preferably, at least one of the first and the second conductor element is equipped with an insulating layer towards the operation space for minimizing effects of parasitic resistivity of the target pharmaceutical sample on the measurement. This insulating layer may further help to increase the lifetime of the respective conductor element. Also, it may help to prevent contamination of the target pharmaceutical sample. Still further, it may prevent or reduce dust build up on the sensor. Finally, it may also allow for easier cleaning of the sensor and particularly its conductor elements.

Preferably, the solid fraction sensor comprises a reference third conductor element and a reference fourth conductor element together establishing a reference capacitor, wherein the controller of the solid fraction sensor is adapted to being responsive to a difference between an output of a measuring capacitor established by the first conductor element and the second conductor element and an output of the reference capacitor. By providing such reference capacitor the influence of the environmental and operating conditions, such as temperature, humidity or the like, on the sample measurement can be reduced or minimized. In particular, it may allow compensation in situation where the calibration curve does not correspond to the operating conditions and, thus, the sensing may be inaccurate.

Preferably, the first conductor element and/or the second conductor element of the solid fraction sensor has a surface area adjacent to the operation space in a range of between 1 mm$^2$ and 10,000 mm$^2$ or preferably between 10 mm$^2$ and 1,000 mm$^2$.

Preferably, the solid fraction sensor establishes a sensor circuit which operates with a dynamic range of 0 Picofarad (pF) to 1,000 pF, preferably of 0 pF to 100 pF and particularly of 0 pF to 10 pF. The sensor circuit preferably operates with a sensitivity of less than 1,000 Femtofarad (fF), preferrably less than 100 fF and particularly less than 10 fF.

Preferably, the solid fraction sensor comprises a distance measuring unit adapted to measure a distance between the first conductor element and the second conductor element. By such distance measuring unit the thickness or other also another dimension of the target pharmaceutical sample can be determined.

Preferably, at least one of the first conductor element and the second conductor element is a roll of a roll press arrangement. The roll press arrangement can be a roller compactor for pressing a powder mixture of the target pharmaceutical sample into a ribbon. A typical roller compactor can comprise two rolls, which press the powder into the ribbon. By embodying at least one of the rolls to be displaced towards the other roll a thickness of the ribbon can be defined or adjusted. Therefore, the displacable roll may achieve to measure or determine the thickness of the target pharmaceutical sample.

In a preferred embodiment of the use according to the invention, the solid fraction sensor involved is a solid fraction sensor according to the invention as described above.

BRIEF DESCRIPTION OF THE DRAWINGS

The use of a solid fraction sensor to evaluate a solid fraction of a target pharmaceutical sample and the solid fraction sensor according to the invention are described in more detail herein below by way of exemplary embodiments and with reference to the attached drawings, in which.

DESCRIPTION OF EMBODIMENTS

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
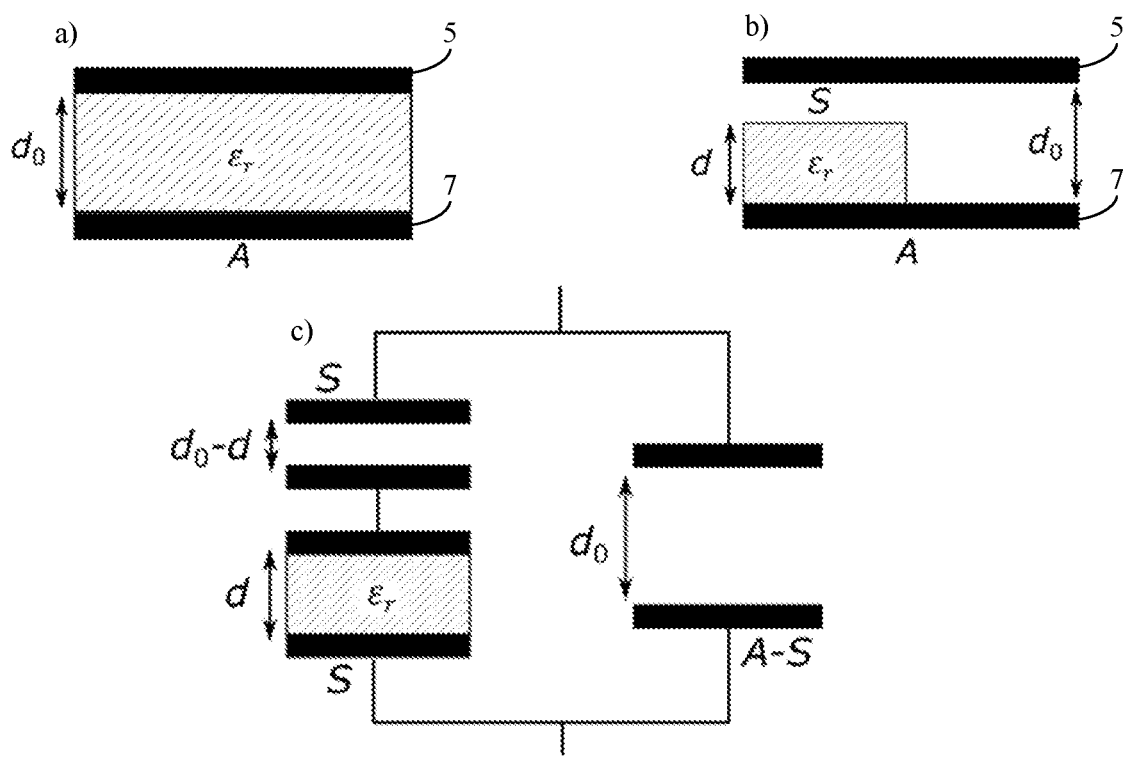
FIG. 1a,b,c shows an arrangement of a capacitor completely filled with a dielectric, a capacitor partially filled with a dielectric and an equivalent circuit diagram for a theoretical evaluation.

By reference to FIG. 1a,b,c a theoretical evaluation of capacitive sensing is illustrated. Capacitive sensing is a non-contact sensing widely used in many industries, including automotive, oil and gas, medical diagnostics or consumer electronics, and pharmaceutical manufacturing. In general, capacitive sensing is applicable to both conductors and non-conductors. It finds typical use as proximity and displacement sensors. Capacitive sensors are rather inexpensive, especially in comparison to spectroscopy systems, and their simple electronic nature makes them adept for online/inline implementation in manufacturing processes.

Capacitive sensing is also suitable to characterize non-conductive material properties, i.e. dielectrics. Material passing through the gap of the capacitive sensor changes the capacitance of the sensor. When the gap in the capacitor is kept constant, the sensor output will be linked to the change in the thickness, density or composition of the material. If two of these properties are kept constant, the third can be deducted from the measurement. Thus, having a material of homogeneous composition and thickness, its density can be deducted from the sensor output. With a simple calibration, this can be converted into the porosity of the material.

FIG. 1a shows an arrangement of a capacitor completely filled with a dielectric 12 between a first conductor element 5—in the following also called electrode 5—and a second conductor element 7—in the following also called electrode 7. Both electrodes 5, 7 have the same surface size A like the dielectric between them, which dielectric has a thickness of $d_0$ and a permittivity of $\varepsilon_r$. The capacitance C of simple parallel plates is governed by $$C = \frac{\varepsilon_o \varepsilon_r A}{d_0} \quad \text{(Eq. 1)}$$

Here $\varepsilon_0$ is the permittivity of vacuum ($\varepsilon_0$=8.85149 pF/m), $\varepsilon_r$ is the relative permittivity of a material between electrodes ($\varepsilon_r$=1 for air), A is the surface area of the electrodes and do is the distance between the electrodes 5, 7. In order to evaluate the relative permittivity of the material of interest, namely the dielectric, one would normally first obtain the capacitance $C_0$ of empty sensor and capacitance C of sensor fully filled with the material of interest. From the difference between these two, $\Delta C=C-C_0$, one can express the relative permittivity of the material as:

$$\varepsilon_r = 1 + \frac{\Delta C d_0}{\varepsilon_0 A} \quad \text{(Eq. 2)}$$

If the dielectric sample fills the full thickness of the sensor but does not cover the full area A (not shown), the resulting sensor can be represented by two capacitors in series, one filled with vacuum (air) and another with the sample. The change in capacity is influenced only by the covered surface area S (corresponding to sample surface area), hence one can simply adapt Eq. 2 as $$\varepsilon_r = 1 + \frac{\Delta C d_0}{\varepsilon_0 S} \quad \text{(Eq. 3)}$$

It is to note that, within the approximation of homogeneous electric field between the electrodes (i.e. far from the sensor edges), the position of the sample on the electrode does not matter.

A further generalization is necessary in case that the sample does not fill the full thickness of the sensor, as shown in FIG. 1b. The resulting air gap can be represented by two capacitors in series, one filled with air and another with the material of interest, see also FIG. 1c with the corresponding equivalent circuit diagram. It is beneficial to define thickness fraction, where d corresponds to the sample thickness. The relative permittivity of the material with thickness $d<d_0$ can be then expressed as $$\varepsilon_r = 1 + \left(\frac{d}{d_0}\frac{\varepsilon_0 S}{\Delta C d_0} + \frac{d}{d_0} - 1\right)^{-1} \quad \text{(Eq. 4)}$$

Figure 2:
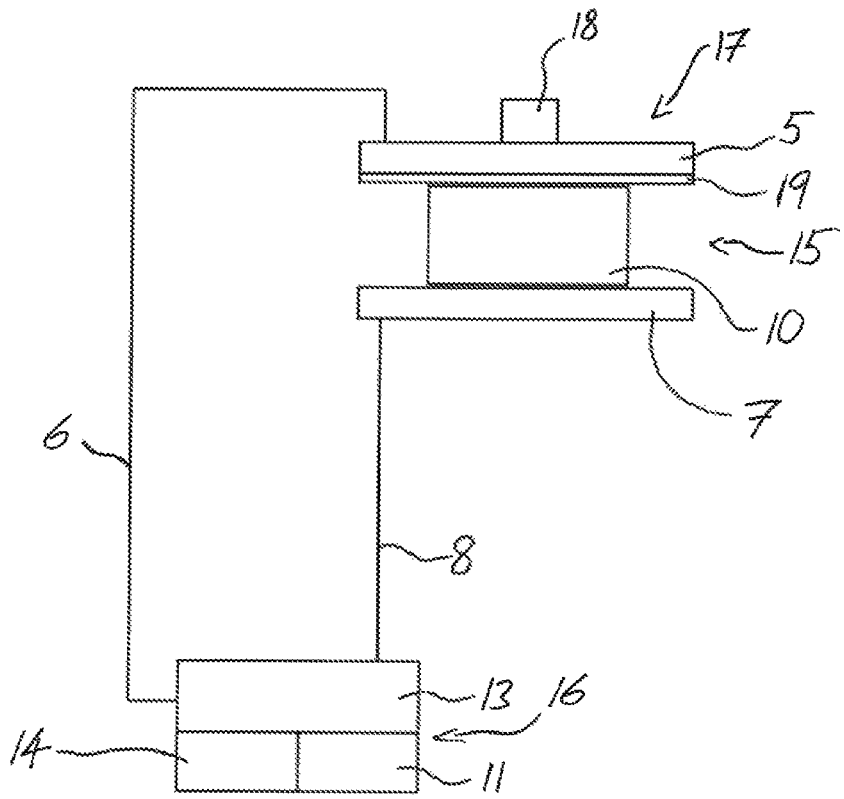
FIG. 2 shows an embodiment of the solid fraction sensor according to the invention for the use with a tablet as a target pharmaceutical sample.

With a view to FIG. 2 the following sensitivity estimation can be determined. A change in sample porosity will result in change in the sample relative permittivity. The non-trivial part is finding a suitable circuitry that allows sensitive enough detection of changes in the relative permittivity. For example, consider a sensor with 3 mm gap between the electrodes 5 and 7 being filled with a 10 mm diameter and 2 mm thick non-porous tablet made of microcrystalline cellulose, which has relative permittivity $\varepsilon_r$=5.6 at 58% relative humidity and 22° C. Using Eq. 1, the increase in the sensor capacitance in the presence of tablet would be approximately 1.6 pF. If a drop in the solid fraction results in a drop of relative permittivity by e.g. 1%, the expected drop in the sensor capacitance would be approx. 20 fF. Hence, the sensing circuit has to be able to detect the capacitance with a few fF accuracy for any practical application as a porosity sensor for solid dosage forms.

In FIG. 2 the pharmaceutical target sample is a tablet 10, which is located in the operation space 15 between a first conductor element 5 and a second conductor element 7 of the solid fraction sensor 17. An energy source 13 is connected to the first and second conductor element 5, 7 via a cable 6 respectively via a cable 8. A controller 11 is adapted to adjust a strength of the electric field in the operation space 15 and furthermore, the controller 11 has a data storage 14 in which calibration data is stored.

According to the invention the controller 11 can be adapted to determine the capacitance by a capacitance-to-digital conversion based on the known sigma-delta modulation.

Alternatively, the solid fraction sensor 17 adapted to measure a discharge time and to determine the capacitance by using the measured discharge time, wherein the solid fraction sensor 17 can be implemented as or comprise a PICO-CAP converter.

Furthermore, the solid fraction sensor comprises a displacement structure 18, wherein at least one of the first conductor element 5 and the second conductor element 7 is mounted to the displacement structure 18 such that the first conductor element 5 and the second conductor element 7 are movable relative to each other. By moving the first conductor element 5 and the second conductor 7 relative to each other, the size of the operation space 15 can be adjusted. For example, it can be achieved that the conductor elements preferably slightly contact an object arranged in the operation space 15. Thereby, the occurrence of free space, namely the air gap between the conductor elements 5, 7 and the tablet 10 can be reduced or minimized such that the accuracy of the solid fraction determination can be increased or optimized.

A thickness measuring unit (not shown in the Fig.) is adapted to measure a thickness of the tablet 10 positioned in the operation space 15, wherein the thickness measuring sensor comprises a distance capacitance sensor.

The first conductor element 5 and the second conductor element 7 is equipped with an insulating layer 19 towards the operation space 15 for minimizing effects of parasitic resistivity of the tablet 10 on the measurement. It may further help to increase the lifetime of the respective conductor element 5, 7. Also, it may help to prevent contamination of the tablet 10. Still further, it may prevent or reduce dust build up on the solid fraction sensor 17. Finally, it may also allow for easier cleaning of the solid fraction sensor 17 and particularly its conductor elements 5, 7.

Figure 3A:
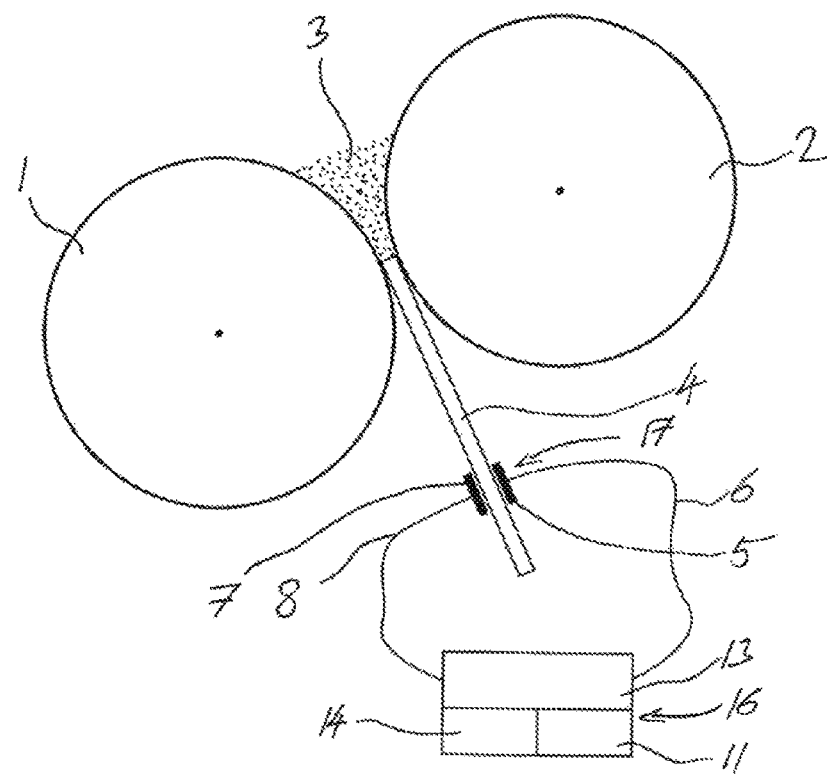
FIG. 3a,b,c shows three further embodiments of the solid fraction sensor for the use with a ribbon compressed out of a powder as a target pharmaceutical sample

In FIG. 3a,b,c another intended application of the solid fraction sensor according to the invention is shown in the measurement of ribbons 4 prepared by roller compaction before they are milled. A typical roller compaction contains two rolls 1 and 2 which press powder 3 into a ribbon 4. By embodying at least one of the rolls 1, 2 to be displaced towards the other roll 1, 2, a thickness of the ribbon 4 can be defined or adjusted. Thereby, an expansion coefficient of the material of the pharmaceutical material can be used for determining the thickness, where appropriate. The ribbon 4 is then milled into granules. The solid fraction of the ribbon 4 influences both hardness and size of the granules. It is therefore highly relevant to the bioavailability of the final pharmaceutical products via dissolution and disintegration characteristics.

In FIG. 3a,b,c a possible implementation of the solid fraction sensor 17 within the roller compactor 20 is outlined. In an ideal case, a representative sample of ribbon 4 is produced without being stuck or keyed to any of the rolls 1, 2. In such circumstances, a similar solid fraction sensor 17 to one shown in FIG. 2 can be used and the ribbon 4 can be fed between the electrodes 5, 7 as shown in FIG. 3a.

Figure 3B:
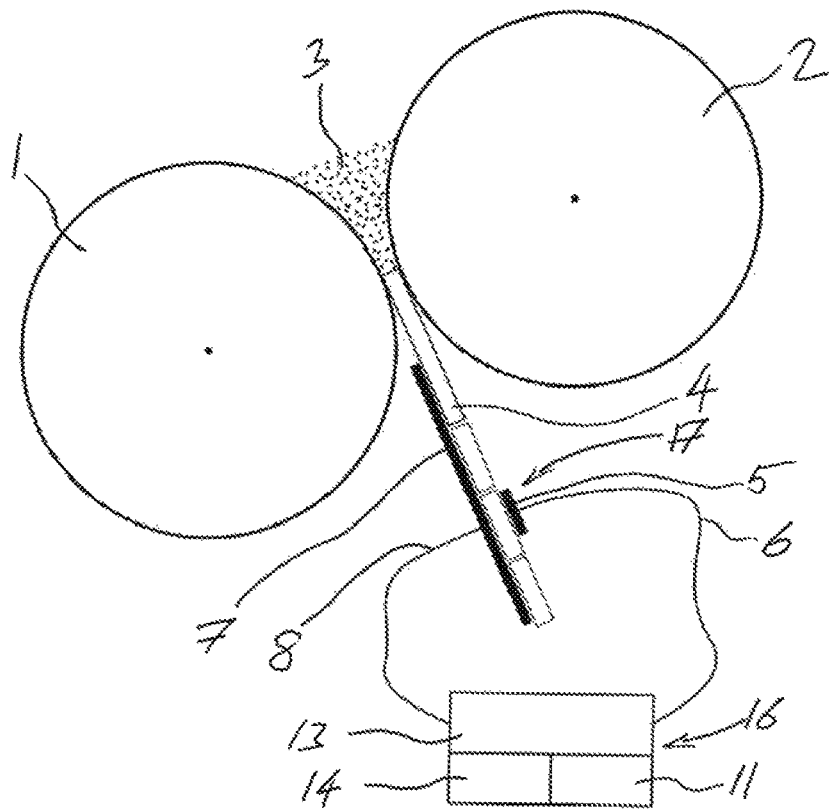

In practice, the ribbons 4 may not always be strong enough and break. In such cases, the ground electrode 7 can be extended and serve as a support, as shown in FIG. 3b. Alternatively, a mechanical support to collect and guide the ribbon 4 can be added to the design, with the electrode 7 implemented within such support. The sensing area will be defined by the solid fraction sensor electrode 5.

Figure 3C:
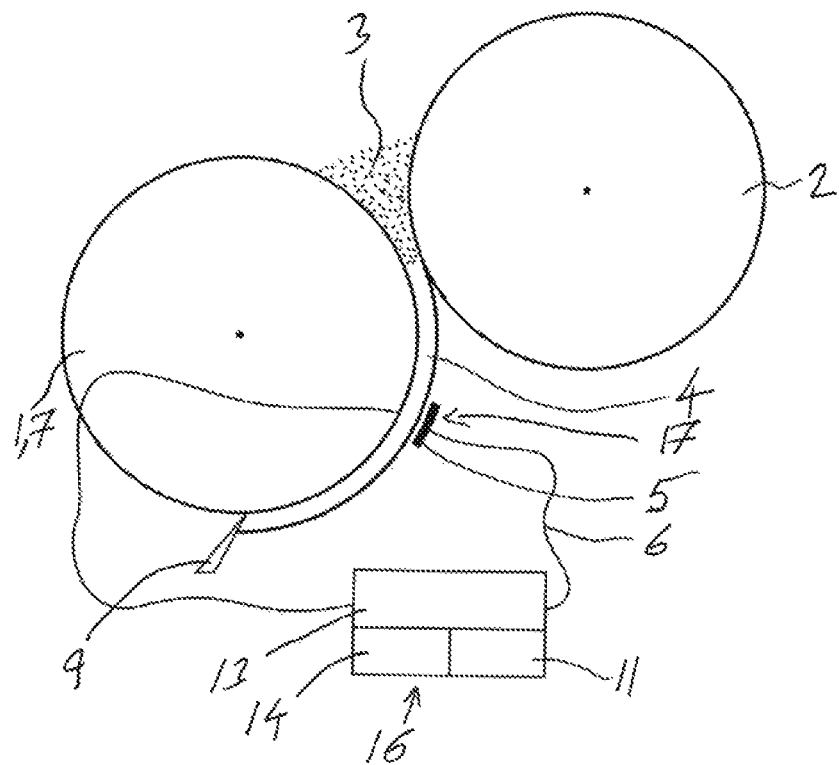

When a collar is applied to the roll 1, the ribbons 4 have a strong tendency to remain keyed to the roll 1 and have to be scrapped off by a scraper 9 as shown in FIG. 3c. In such cases, the roll 1 can be used as electrode 7 and the solid fraction sensor requires only one custom-made electrode 5. The sensing area will be again defined by the sensor electrode 5. In this case, the sensor electrode 5 may be curved to limit the inhomogeneity in the generated electric field.

In all cases, the solid fraction sensor 17 can be connected as a floating sensor (with the ground electrode floating) or as a grounded sensor (with the ground electrode grounded). When the ground electrode is connected as a floating electrode, one of the electrodes can be used for the excitation and another for the read-out. When the ground electrode is grounded, the setup requires a switch (not shown) to allow for use of the sensor electrode for both excitation and read-out. The latter is practically useful for the cases described in FIGS. 3b and 3c. Here either the support or the roll should be grounded to minimize the parasitic capacitive and resistive signals from the machinery and other external disturbances.

Figure 4:
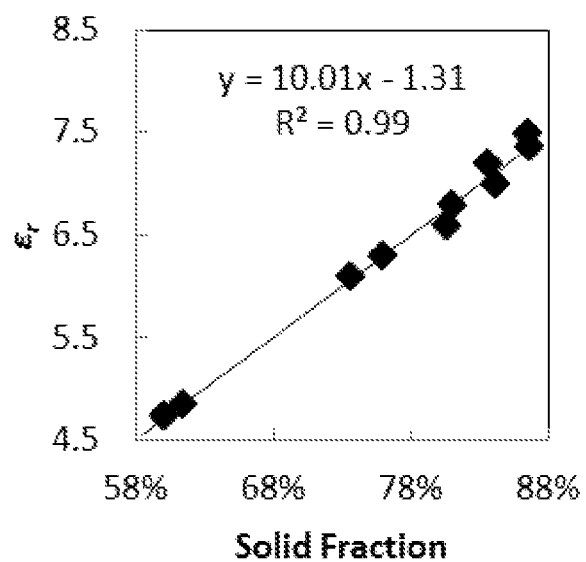
FIG. 4 shows an example of a calibration curve.

FIG. 4 shows an example of a calibration curve in which pairs of permittivity and corresponding solid fraction ratio of a reference pharmaceutical substance are displayed. In particular, in the example calibration curve, a calibration obtained at uniform operating conditions on tablets with different thickness after thickness correction is shown.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A method of evaluating a solid fraction of a target pharmaceutical sample by means of a solid fraction sensor, wherein the solid fraction sensor has a first conductor element, a second conductor element, an operation space and an energy source arranged to generate an electric field in the operation space by means of the first conductor element and the second conductor element, the method comprising:
   positioning the target pharmaceutical sample in the operation space of the solid fraction sensor;
   determining a capacitance between the first and second conductor elements with the target pharmaceutical sample located in the operation space; and
   converting the determined capacitance together with information about a composition of a reference pharmaceutical sample having essentially the same dielectric properties as the target pharmaceutical sample and about a thickness of the reference pharmaceutical sample into a solid fraction of the target pharmaceutical sample,
   wherein the information about the composition of the reference pharmaceutical sample comprises pairs of permittivity of the reference pharmaceutical sample and a corresponding solid fraction ratio of the reference pharmaceutical sample.

2. The method of claim 1, wherein the target pharmaceutical sample is bounded or wherein the target pharmaceutical sample is unbounded.

3. The method of claim 1, further comprising adjusting a strength of the electric field in the operation space.

4. The method of claim 1, wherein the information about the composition of the reference pharmaceutical sample and about the thickness of the reference pharmaceutical sample is a calibration curve.

5. The method of claim 1, wherein the capacitance is determined by a capacitance-to-digital conversion, preferably by applying a sigma-delta modulation to determine the capacitance, or wherein a discharge time is measured and the capacitance is determined by using the measured discharge time.

6. The method of claim 1, wherein a charge-balancing circuit is used to measure the capacitance.

7. The method of claim 1, wherein at least one of the first conductor element and the second conductor element is displaced to adjust the operation space.

8. The method of claim 1, further comprising measuring a thickness of the target pharmaceutical sample positioned in the operation space.

9. The method of claim 1, further comprising:
   positioning the target pharmaceutical sample in a further operation space of the solid fraction sensor or a further solid fraction sensor, having a further first conductor element, a further second conductor element, wherein the further operation space and a further energy source are arranged to generate an electric field in the further operation space by means of the further first conductor element and the further second conductor element;
   determining a further capacitance of the target pharmaceutical sample located in the further operation space;
   converting the determined further capacitance together with the information about the composition of the reference pharmaceutical sample and about the thickness of the reference pharmaceutical sample into a further solid fraction of the target pharmaceutical sample; and determining a solid fraction distribution of the solid fraction of the target pharmaceutical sample and the further solid fraction of the target pharmaceutical sample, wherein the operation space and the further operation space preferably are positioned neighbouring each other such that different parts of the target pharmaceutical sample are involved when determining the capacitance and the further capacitance of the target pharmaceutical sample.

10. The method of claim 1, further comprising:

positioning the target pharmaceutical sample in a reference operation space of a reference solid fraction sensor having a reference first conductor element, a reference second conductor element, the reference operation space and a reference energy source arranged to generate an electric field in the reference operation space by means of the reference first conductor element and the reference second conductor element;

determining a reference capacitance of the target pharmaceutical sample located in the reference operation space;

converting the determined reference capacitance together with the information about the composition of the reference pharmaceutical sample and about the thickness of the reference pharmaceutical sample into a reference solid fraction of the target pharmaceutical sample; and comparing the solid fraction of the target pharmaceutical sample to the reference solid fraction of the target pharmaceutical sample in its solid state.

11. The method of claim 1, further comprising measuring a distance between the first and second conductor elements.

12. The method of claim 1, wherein at least one of the first and second conductor elements is a roll of a roll press arrangement.

13. The method of claim 1, wherein the solid fraction sensor, preferably being electromagnetically shielded, further comprises:

a controller adapted to determine a capacitance of the target pharmaceutical sample located in the operation space; wherein the controller comprises calibration data of the reference pharmaceutical sample having the essentially same dielectric properties as the target pharmaceutical sample; and the calibration data comprises composition data about the composition of the reference pharmaceutical sample and thickness data about the thickness of the reference pharmaceutical sample comprising pairs of permittivity of the reference pharmaceutical sample and the corresponding solid fraction ratio of the reference pharmaceutical sample; the method further comprising the steps of:

converting, via the controller, the calibration data and the determined capacitance into solid fraction data of the target pharmaceutical sample; and generating, via the controller, a solid fraction signal representing the solid fraction data.

14. A solid fraction sensor, preferably being electromagnetically shielded, comprising:

a first conductor element;
a second conductor element;
an operation space;
an energy source arranged to generate an electric field in the operation space by means of the first conductor element and the second conductor element; and a controller adapted to determine a capacitance of a target pharmaceutical sample located in the operation space, wherein the controller comprises calibration data of a reference pharmaceutical sample having the essentially same dielectric properties as the target pharmaceutical sample, the calibration data comprises composition data about the composition of the reference pharmaceutical sample and thickness data about the thickness of the reference pharmaceutical sample comprising pairs of permittivity of the reference pharmaceutical sample and a corresponding solid fraction ratio of the reference pharmaceutical sample, the controller is adapted to convert the calibration data and the determined capacitance into solid fraction data of the target pharmaceutical sample, and the controller is adapted to generate a solid fraction signal representing the solid fraction data.

15. The solid fraction sensor of claim 14, wherein the energy source is connected to at least one of the first conductor element and the second conductor element.

16. The solid fraction sensor of claim 14, wherein the controller is adapted to adjust a strength of the electric field in the operation space.

17. The solid fraction sensor of claim 14, wherein the controller has a data storage in which the calibration data is stored.

18. The solid fraction sensor of claim 14, wherein the first conductor element and the second conductor element are metallic and plate-like shaped.

19. The solid fraction sensor of claim 14, wherein the controller is adapted to determine the capacitance by a capacitance-to-digital conversion, wherein the controller preferably is adapted to apply sigma-delta modulation to determine the capacitance.

20. The solid fraction sensor of claim 14, wherein the controller is adapted to measure a discharge time and to determine the capacitance by using the measured discharge time.

21. The solid fraction sensor of claim 14, wherein the controller is adapted to determine the capacitance by using a charge-balancing method.

22. The solid fraction sensor claim 14, further comprising a displacement structure, wherein at least one of the first conductor element and the second conductor element is mounted to the displacement structure such that the first conductor element and the second conductor element are movable relative to each other.

23. The solid fraction sensor of claim 14, wherein the operation space is a gap separating the first conductor element and the second conductor element.

24. The solid fraction sensor of claim 14, further comprising a thickness measuring unit adapted to measure a thickness of the target pharmaceutical sample, wherein the thickness measuring unit preferably is adapted to measure the thickness of the target pharmaceutical sample when being positioned in the operation space, and wherein the thickness measuring unit preferably comprises a distance capacitance sensor.

25. The solid fraction sensor of claim 14, wherein at least one of the first conductor element and the second conductor element is equipped with an insulating layer towards the operation space.

26. The solid fraction sensor of claim 14, further comprising a distance measuring unit adapted to measure a distance between the first conductor element and the second conductor element.

27. The solid fraction sensor of claim 14, wherein at least one of the first conductor element and the second conductor element is a roll of a roll press arrangement.

* * * * *